(12) United States Patent
Salo et al.

(10) Patent No.: US 7,194,305 B1
(45) Date of Patent: *Mar. 20, 2007

(54) CARDIAC RHYTHM MANAGEMENT SYSTEM WITH OPTIMIZATION OF CARDIAC PERFORMANCE USING HEART RATE

(75) Inventors: Rodney W. Salo, Fridley, MN (US); Lawrence S. Baumann, Bloomington, MN (US); Kenneth L. Baker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/545,536

(22) Filed: Apr. 7, 2000

(51) Int. Cl.
*A61N 1/00* (2006.01)
(52) U.S. Cl. .......................................................... 607/9
(58) Field of Classification Search .................. 607/9, 607/17, 26
See application file for complete search history.

(56) References Cited

U.S. PATENT DOCUMENTS

| 4,674,518 A | 6/1987 | Salo |
| 4,686,987 A | 8/1987 | Salo et al. |
| 4,733,667 A | 3/1988 | Olive et al. |
| 5,179,949 A | 1/1993 | Chirife |
| 5,312,452 A | 5/1994 | Salo |
| 5,330,511 A | 7/1994 | Boute |
| 5,334,222 A | 8/1994 | Salo et al. |
| 5,466,245 A | 11/1995 | Spinelli et al. |
| 5,487,752 A | 1/1996 | Salo et al. |
| 5,540,727 A | 7/1996 | Tockman et al. |
| 5,713,930 A | 2/1998 | van der Veen et al. |
| 5,716,383 A | 2/1998 | Kieval et al. |
| 5,792,203 A | 8/1998 | Schroeppel |
| 5,800,465 A | 9/1998 | Thompson et al. |
| 5,800,471 A * | 9/1998 | Baumann ..................... 607/25 |
| 6,044,298 A | 3/2000 | Salo et al. |

OTHER PUBLICATIONS

"Usefulness of Physiologic Dual-Chamber Pacing In Drug-Resistant Idiopathic Dilated Cardiomyopathy", The American Journal of Cardiology, Hochleitner, Hortnagl, Choi-Keung Ng, et al., vol. 66, Jul. 15, 1990, pp. 198-202.
"Hemodynamic Effect Of Physiological Dual Chamber Pacing In A Patient With End-Stage Dilated Cardiomyopathy: A Case Report", Hajime Kataoka, PACE, vol. 14, Sep. 1991, pp. 1330-1335.

* cited by examiner

*Primary Examiner*—Mark Bockelman
(74) *Attorney, Agent, or Firm*—Schwegman, Lundberg, Woessner, & Kluth

(57) ABSTRACT

A cardiac rhythm management device includes a dual chamber pacemaker, especially designed for treating congestive heart failure by pacing a plurality of sites. The device incorporates a program microcontroller which is operative to adjust the pacing mode and inter-site delay of the pacemaker so as to achieve optimum hemodynamic performance. Atrial cycle lengths measured during transient (immediate) time intervals following a change in the mode inter-site delay are signal processed and a determination can then be made as to which particular configuration yields the optimum performance. Performance is optimized when the patient is at rest and when the patient exercises so that a rate-adapted dynamic value of the optimum performance can be applied.

13 Claims, 8 Drawing Sheets

$BL_1\ BL_2\ ...BL_{13},\ BL_{14}\ BL_{15}\ C,\ C,\ C,\ C,\ C,\ BL_1\ BL_2\ BL_3\ ...BL_{15}$

|——MAX. AND MIN.——|

|———MEAN———|

— BEAT OF MAX. VALUE $BL,\ BL,\ BL,\ ...BL,\ BL,\ BL\ C,\ C,\ C,\ C,\ C,\ BL,\ BL,\ BL,\ BL\ ...BL$

|———MAX.———|

|———MIN.———|

CARDIAC RHYTHM MANAGEMENT SYSTEM WITH OPTIMIZATION OF CARDIAC PERFORMANCE USING HEART RATE

BACKGROUND OF THE INVENTION

I. Field of the Invention

This invention relates generally to implantable cardiac rhythm management devices, and more particularly to a method for establishing an optimum pacing mode and delay parameters for multiple pacing sites in a dual chamber implantable programmable pacemaker.

II. Related Art

An earlier patent to Baumann, a co-inventor herein, U.S. Pat. No. 5,800,471, assigned to the assignee of the present invention, the teachings of which are hereby incorporated by reference, explains that cardiac pacing can be used to improve hemodynamics in congestive heart failure (CHF) patients. One recognized and accepted indication of hemodynamic performance is reflected in the patient's pulse pressure (PP) which is defined as the difference between systolic aortic pressure and diastolic aortic pressure. PP could be used ot optimize the pacing parameters in applying CHF therapy, however, this would require the use of a suitably positioned pressure sensor.

The Baumann '471 patent recognizes that an indirect indication of PP can be derived from the patient's atrial cycle length (ACL), which is the duration of the interval between consecutive P-waves in an ECG signal. The earlier Baumann patent discloses a method for using ACL to optimize CHF therapy parameters that involves looking at a transient sequence in which, after a period of intrinsic cardiac activity, a short predetermined sequence of pacing stimuli is delivered to the patient's heart. Any subsequent transient increase in measured ACL provides an indication of the therapy's effectiveness over intrinsic cardiac activity. Likewise, a subsequent transient decrease in measured ACL is indicative that the pacing therapy is non-beneficial.

In applying the methodology to an implantable, microprocessor-based controller of the type typically used in a programmable dual-chamber pacemaker, the device is made to cycle through transient paced beats with different pacing mode and AV delay configurations. Each such configuration is defined to be a group of consecutive beats with the same paced AV delay and the same pacing mode (right ventricular, left ventricular or biventricular pacing). Each of the configurations is immediately preceded by a group of baseline beats. In the disclosed arrangement, three different pacing modes and five different AV delays are used, with each such delay being shorter than a previously measured value of the intrinsic AV delay. The particular mode/AV delay combination that results in the largest increase in ACL is then programmed into the pacemaker to thereby optimize hemodynamic performance of the patient's heart. To avoid inaccuracies due to noise, the algorithm described in the Baumann '471 patent is made to vary the order of therapy; randomization and averaging techniques are then used to extract data from repeated tests.

While the above approach has proved to be a useful tool, it does not take into account variations in time between pulse events with respect to pacing at multiple sites. It is common to stimulate both ventricle chambers, for example, and particularly the left ventricle can be provided with a plurality of sequentially paced sites. Each of these is operated using a timed delay sequence which may be selected from a menu of sequence timings which itself may change as data regarding patient history accumulates. Thus, if all paced sites could be integrated into an optimal pacing rhythm, additional benefit could be accorded the patient.

SUMMARY OF THE INVENTION

The foregoing features and advantages of the invention are achieved by providing an improved method for optimizing the inter-site delay and pacing mode configuration of an implanted, programmable pacemaker when treating CHF patients. The pacemaker involved is of the dual chamber type that includes an atrial sense circuit, a ventricular sense circuit and a pulse generator for applying cardiac stimulating pulses selectively to the right ventricular chamber, the left ventricular chamber or both chambers sequentially (biventricular pacing). A plurality of pacing sites may be located in a single chamber, usually the left ventricle, and these are also paced using a time variable delay sequence. The patient's intrinsic atrial depolarization events are tracked and from such events the ACL is measured over a first predetermined number of heartbeats, $N_1$, to establish a baseline value. At least one of the inter-site delay interval and the pacing mode configuration is changed for a predetermined number of stimulated heartbeats, $N_2$ and, again, the ACLs between successive paced beats is measured. These steps are repeated in iterative cycles until all of the preprogrammed inter-site delay intervals and ventricular chamber options have been utilized. Subsequently, a comparison is made to determine which configuration of pacing mode and inter-site delay values resulted in the maximum increase ACL and those values are then programmed into the pacemaker. In that maximum increase of ACL correlates with maximum increase of PP, hemodynamic performances are thereby optimized. Additional performance parameters may also be used to correlate to PP or other relevant indicators of cardiac performance, these performance parameters include: ventricular volumes, blood flow velocity, total acoustic noise, and direct measurement of pressure.

As used herein, the terms "site-to-site delay" and "inter-site delay" mean the time interval between any sequential pacing events in the same cardiac cycle regardless of whether they occur in different or the same chamber. Thus, AV, V—V, $V_1$-$V_2$ (same chamber), A—A etc. may be represented depending on the pacing configuration.

The optimization determination is first made with the patient at rest to determine the most advantageous pacing mode. Thereafter, a one or more additional or periodic determinations can be implemented with the patient exercising or otherwise in an active state employing the technique to determine the optimum site-to-site delays and enable dynamic site-to-site delays to be implemented based on activity level. This empowers the system to implement dynamic site-to-site delays on its own based on an internal monitoring system.

DESCRIPTION OF THE DRAWINGS

The foregoing features, objects and advantages of the present invention will become apparent to those skilled in the art from the following detailed description of a preferred embodiment, especially when considered in conjunction with the accompanying drawings in which.

DESCRIPTION OF THE PREFERRED EMBODIMENT

The present invention provides a method for establishing an optimum pacing mode and delay parameters for multiple pacing sites in a dual chamber implantable programmable pacemaker. The invention is described below in the context of utilizing atrial cycle length as the measured parameter for assessing the efficacy of the pacing mode and delay parameters. One skilled in the art will recognize that a variety of alternative performance parameters may be used to determine the efficacy of the pacing mode and pacing parameter. These performance parameters include ventricular volumes, blood flow velocity, total acoustic noise, and direct measurement of pressure.

These performance parameters may be assessed with a number of specific methods. That is, there are a many ways of assessing cardiac function including systolic function and/or diastolic function of a heart, that may be incorporated into an implantable microcontroller based cardiac pacemaker. Thus, for example, the cardiac function sensing circuit may measure intracardiac impedance variations due to the influx and outflow of blood from one of the ventricular chambers. This method is discussed in U.S. Pat. Nos. 4,686,987 and 4,674,518 to Salo, which are hereby incorporated by reference. Using this method it is possible to assess ventricular volume, stroke volume, cardiac ouput and derivatives of these parameters.

The cardiac function sense circuit may also comprise an accelerometer for measuring heart sounds or total acoustic noise (TAN). The TAN corresponding to optimal mechanical timing of the heart may be measured using an implantable accelerometer as disclosed in U.S. Pat. No. 6,044,298 to Salo et al, hereby incorporated by reference. It is also contemplated that a micromachined piezoelectric pressure transucer may be mounted on the right or left ventricular pacing lead where it may measure right or left ventricular pressure parameters such as end-diastolic or end systolic pressure or derivatives of these pressures corresponding to ventricular contractility.

The cardiac function sense circuit may also comprise a Doppler flow meter having a flow sensor operatively positioned relative to the aorta or pulmonary artery for measuring peak aortic or pulmonic flow velocity from which measures that are directly correlated to stroke volume and cardiac output may be derived. Similar measurements may be made of mitral or tricuspid flow velocity.

Figure 1:
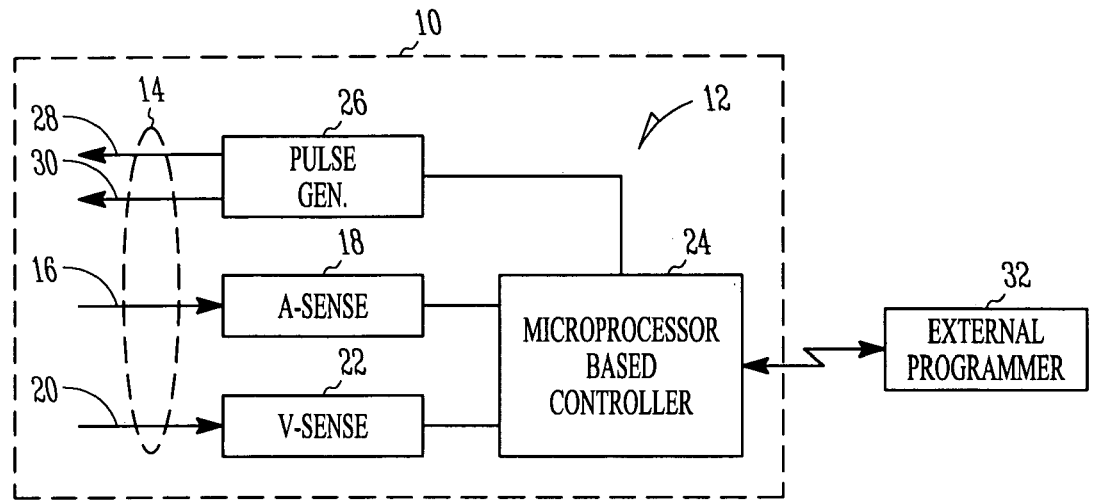
FIG. 1 is a schematic block diagram of a dual chamber pacemaker incorporating a microprocessor-based controller for pacing at a plurality of sites in which the inter-site delay parameters are optimized in accordance with the algorithms disclosed herein.

Referring now to FIG. 1 representing a preferred embodiment, there is shown enclosed by a dashed-line box 10, a cardiac rhythm management device, here depicted as a VDD bradycardia pacemaker 12, which is adapted to be operatively coupled to a patient's heart by means of a conventional pacing lead 14. In particular, an atrial sensing electrode disposed in the right atrium of the heart is coupled by a wire 16 in the lead 14 to an atrial sense amplifier 18. Similarly, a ventricular sensing electrode disposed in the right ventricle is connected by a wire 20 in the lead 14 to a ventricular sense amplifier 22 contained within the pacemaker 12. Thus, when the SA node in the right atrium depolarizes, the resulting signal is picked up by the atrial sense amplifier 18 and applied to a microprocessor-based controller 24 which will be more particularly described with the aid of FIG. 2. Ventricular depolarization signals (R-waves) are likewise amplified by the ventricular sense amplifier 22 and applied as an input to the microprocessor-based controller 24.

The microprocessor-based controller 24 is connected in controlling relationship to a pulse generator 26 to cause a ventricular stimulating pulse to be applied, via conductor 28 in lead 14, to tissue located proximate the apex of the right ventricle (RV) to initiate ventricular depolarization that spreads as a wave across both the right and left ventricles. The pulse generator 26, under control of the microprocessor-based controller 24, can also be made to apply stimulating pulses over a wire 30 in lead 14 to stimulate the heart's left ventricle (LV). If the pacing mode calls for biventricular pacing, the pulse generator 26 is controlled by the microprocessor-based controller 24 to deliver stimulating pulses to sites in both the right and left ventricles (BV). In accordance with contemporary techniques, the left ventricle additionally may be sequentially paced at a plurality of locations (sites).

The microprocessor-based controller 30 controls the timing of stimulating pulses at cardiac sites relative to a selected preceding depolarization signal and to each other to thereby define site-to-site pulsing intervals. The system is capable of pacing in several modes and at variable site-to-site time delays in each mode.

An external programmer 32 is arranged to send data signals transcutaneously to the implanted pacemaker 12 and also to receive signals originating within the pacemaker. In this fashion, a physician is capable of programming such parameters as pacing rate, pacing pulse width, pacing pulse amplitude, sensitivity, AV delay interval, etc., in a fashion known in the art. The external programmer may also be used to receive signals and pass them on to an external monitor (not shown) incorporating a microprocessor and associated memory.

Figure 2:
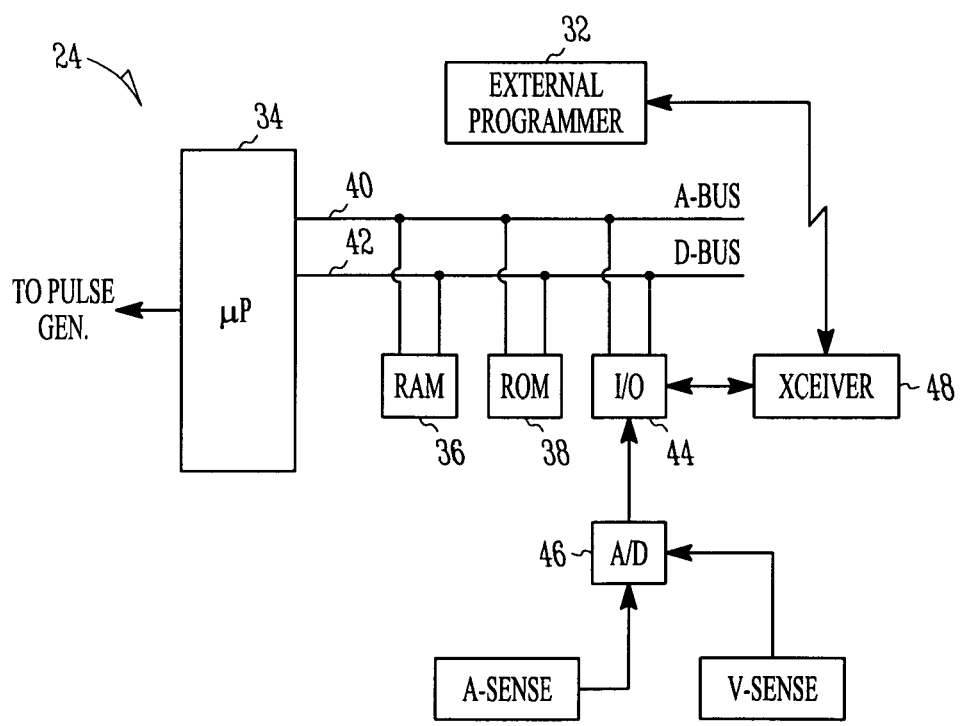
FIG. 2 is a schematic block diagram of the microprocessor-based controller incorporated into the pacemaker of FIG. 1.

FIG. 2 shows a more detailed block diagram of the microprocessor-based controller 24 shown in FIG. 1. It is conventional in its architecture and includes a microprocessor chip 34 and associated RAM and ROM memory modules 36 and 38 connected to it by an address bus 40 and a data bus 42. As is known in the art, the RAM memory 36 is a read/write memory comprising a plurality of addressable storage locations where multi-byte data words and operands used in the execution of one or more programs may be stored for subsequent readout. The ROM memory 38 will typically be used to store the control programs executable by the microprocessor chip 34.

Also connected to the address bus and data bus is an I/O interface module 44. If a separate analog-to-digital converter, as at 46, is utilized rather than an on-board A/D converter forming a part of the microprocessor chip 34, its output will be connected through the I/O module 44 allowing the analog outputs from the atrial sense amplifier 18 and the ventricular sense amplifier 22 to be digitized before being routed to the microprocessor chip 34. If the particular microprocessor employed incorporates an on-board A/D converter (as is somewhat conventional), then the outputs from the A-sense amplifier 18 and V-sense amplifier 22 are applied directly to appropriate inputs of the microprocessor chip 34.

Also coupled to the I/O module 44 is a transceiver 48 that is used to interface the external programmer 32 to the implanted pacer 12. The manner in which an external programmer appropriately placed on the chest wall in proximity to the implanted device is capable of transmitting digitally encoded data therebetween is well known to those skilled in the pacemaker art.

Figure 3:
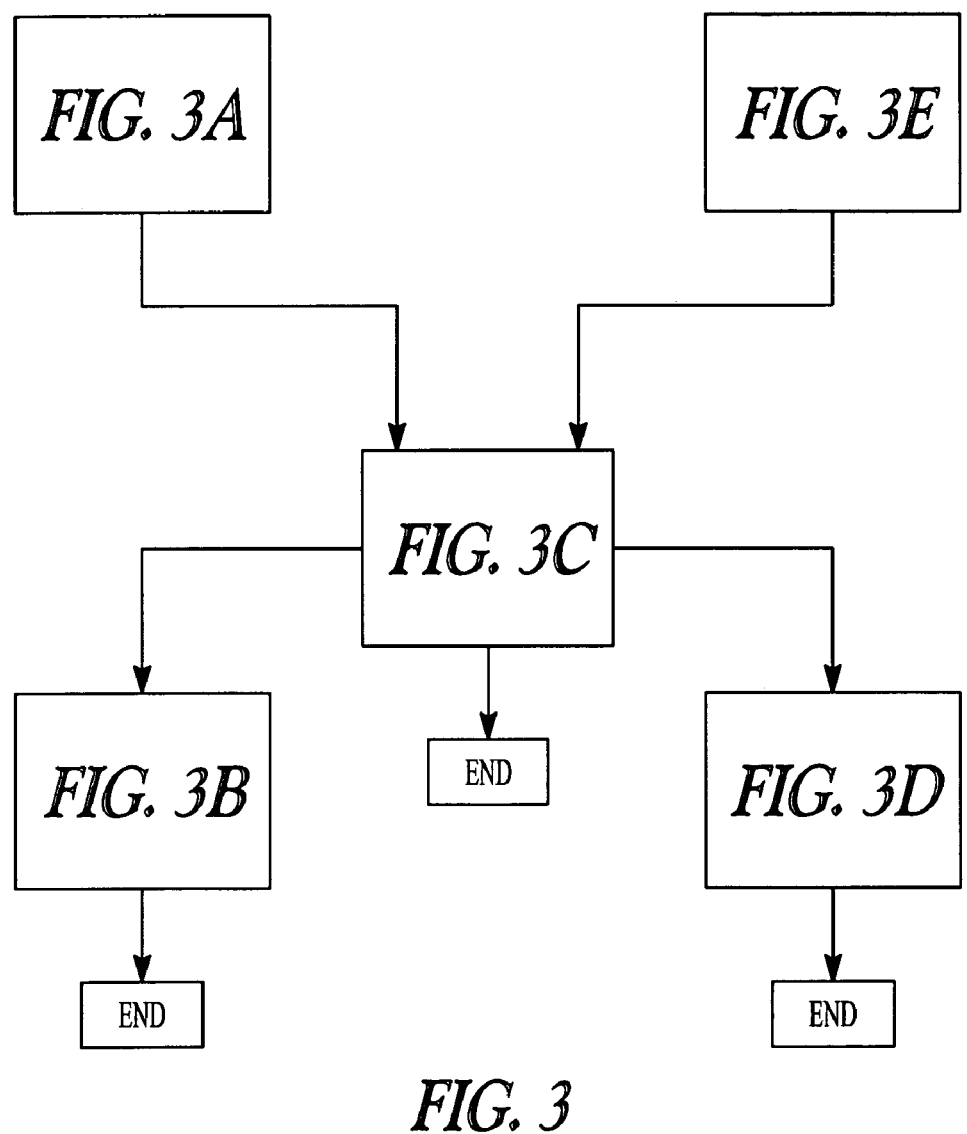
FIGS. 3A, 3B, 3C, 3D and 3E, when arranged as shown in FIG. 3, illustrate a flow diagram for the optimization algorithm of the present invention.

FIGS. 3A, 3B, 3C, 3D and 3E when arranged as shown in FIG. 3 comprise a flow chart of the algorithms executed by the microprocessor 34 in arriving at an optimal pacing mode and inter-site delay combination for a patient in which the system of the present invention is implanted.

Before explaining the steps of the algorithm in detail, a brief overview of the methodology is deemed helpful.

The algorithms can be executed by the microprocessor-based controller in the pacer or in an external microprocessor in the monitor/programmer 32. In the following description, it is assumed that the control algorithms are executed by the microprocessor 34 in the implanted device. The algorithms, using cardiac atrial cycle lengths measured in the VDD pacemaker, determines a patient's optimum pacing mode and inter-site delay configuration, which is the mode (e.g., RV, LV, BV, RV and $LV_1$, $LV_2$, etc.) and inter-site delay during VDD pacing which maximizes cardiac function (e.g., PP) for the patient. The pulse generator 26 is then set to operate at this optimum pacing mode and inter-site delay.

The optimal pacing mode and associated optimum inter-site delays are determined from the maximum (or minimum) value of one of several empirically derived features which are calculated from the atrial cycle lengths. In particular, the atrial cycle lengths immediately following a transition from an intrinsic or paced baseline (BL) to a paced mode, inter-site delay, i.e., during a transient period of the paced mode and inter-site delay, is used. Thus, this invention eliminates the need for a period of waiting for hemodynamic stability to be reached during the paced mode and particular inter-site delay.

The pulse generator will be made to cycle through a predetermined number of intrinsic or paced BL beats followed immediately by paced beats using a first mode and inter-site delay configuration, followed immediately by additional intrinsic or paced BL beats, followed immediately by beats of a second mode and inter-site delay configuration, etc., until all of the possible programmed configurations have been utilized. The ACL between successive beats is computed and stored as an array in the RAM memory of the microprocessor-based controller.

Once the array of ACL values are stored, they are subsequently processed to arrive at values of ACL features. In particular, the array of values may be smoothed using a 3-point moving rectangle window or an 11-point moving Blackman window. Then for each configuration and repeated instances thereof, further computations are made to identify the particular configuration exhibiting the largest average of the smoothed ACL features. It is this configuration that is determined to be the optimum and the pacemaker is then set to operate in this optimum configuration. The automatic selection of optimal mode delay which is found to optimize cardiac function eliminates any need for manual programming of the implanted pacemaker by the physician.

The algorithms of the present invention are based upon a hypothesis that if a transient change in atrial cycle length is large positive, then the transient change in aortic pulse pressure is also large positive. Thus, the largest positive change in atrial cycle length predicts the largest positive change in aortic pulse pressure.

There is a physiological basis for this relationship. A large, sudden increase in the aortic pressure (in this case due to the sudden change from baseline cardiac function to paced mode inter-site delay cardiac function) is sensed by arterial barroreceptors, and the reflex mechanism of the Autonomic Nervous System (ANS) tries to drive the aortic pressure back to its previous stable (in this case, baseline) value by increasing the atrial cycle length. The ANS acts as a negative feedback control system for the aortic pressure.

The paced mode and inter-site delay associated with the largest mean increase in ACL is hypothesized to be the optimum paced mode and inter-site delay for the pacemaker. The optimum is the one that provides a maximum increase in aortic pressure over baseline aortic pressure for the then-current state of activity of the patient. As will also be seen, this may change with increased levels of activity in the patient.

With the foregoing summary in mind, then, attention is directed to the flow charts of FIGS. 3A through 3D. The first step in the algorithm is to derive a baseline. The pulse generator is initially inhibited while intrinsic cardiac activity is sensed such that a value of the patient's intrinsic AV delay and ACL can be measured. Next, the physician may generate a list of all possible combinations of three pacing modes and a predetermined number of inter-site delay values where each of the delay values is set as desired. While a different number of paced inter-site delay values can be selected, arbitrarily and for purposes of explanation of the inventive algorithm, it will be assumed that five different inter-site values are established by the physician. These may include a plurality of pacing sites in the same chamber and/or sites in several chambers. Generally, plural sites will be limited to the left ventricle, however. This leads to 3×5=15 possible configurations as indicated in block 52.

Figure 3A:
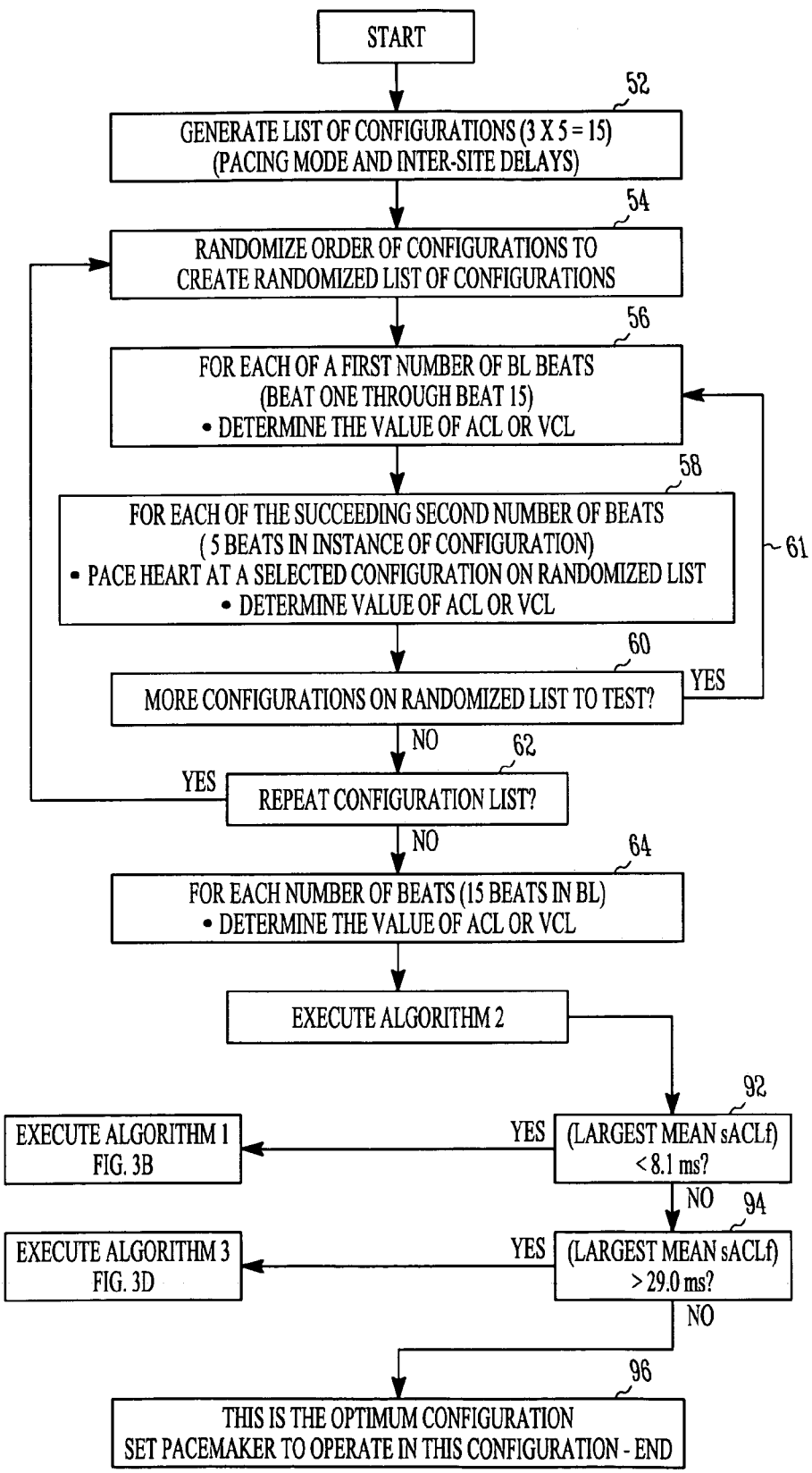

To avoid any influence that the particular order in which the configurations are employed in pacing the patient, the list generated in step 52 is randomized as reflected in block 54 in FIG. 3A.

Again, without limitation, a string of beats with the pulse generator inhibited may be used to establish BL and then for each of these baseline beats, the atrial cycle length between them is determined. As earlier mentioned, rather than using intrinsic inter-site delays to establish BL, the BL can also be at a particular configuration of pacing mode and inter-site delays. In the description to follow, a group of at least 15 sequential beats are generated. The ACL measurement may be performed in the microprocessor by initiating a timer upon the occurrence of a P-wave in the cardiac electrogram and stopping the timer upon detection of the next succeeding P-wave. The ACL value associated with each BL beat is then stored as an array in the RAM memory 36.

Referring again to the block diagram of FIG. 3A, immediately following the last of the beats used in establishing BL, the heart is paced using a selected configuration drawn from the randomized list developed at block 54. Again, without limitation, the second number of beats may equal five. As with the BL beats, the ACL for the paced beats is also determined as reflected in block 58.

A test is next made at block 60 to determine whether all of the 15 possible configurations on the randomized list have been used and the ACL values associated therewith stored in the memory.

If not all of the configuration possibilities have been exhausted, control returns over path 61 to block 56 and the operations reflected in blocks 56 and 58 are repeated until all of the possibilities have been exhausted. So that any anomalies which may have occurred in the measurement of the respective ACL values can be averaged out, steps 54, 56, 58 and 60 are repeated a predetermined number of times, e.g., five times, to obtain additional instances of the configurations that can later be averaged. See decision block 62.

The change in PP caused by the five paced beats in step 58 is immediate. There is no time delay. However, the change in ACL caused by the reflex mechanism of the Autonomic Nervous System in response to this change in PP is not immediate. There is a time delay of several beats. Thus, the delayed change in ACL can occur during the 15 BL beats in step 56 which follow the five paced beats in step 58. Thus, the final 15 or more BL beats in step 64 are needed to follow the final five paced beats in step 58.

Once the raw ACL values have been computed and stored as an array in the RAM memory, further algorithms may be used to process the raw data in arriving at the particular pacing mode-AV delay configuration yielding optimum hemodynamic performance.

Figure 3B:
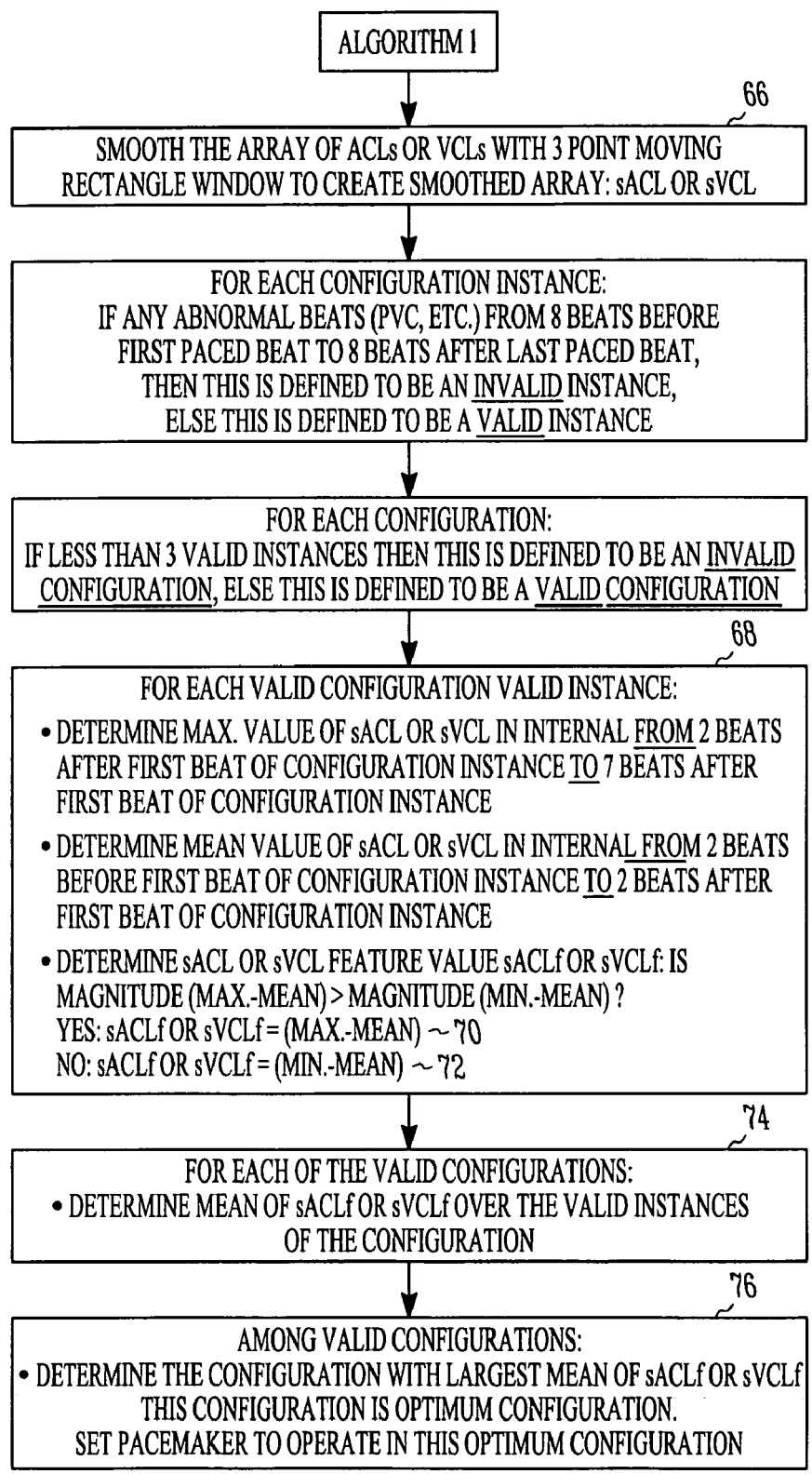
Figure 3C:
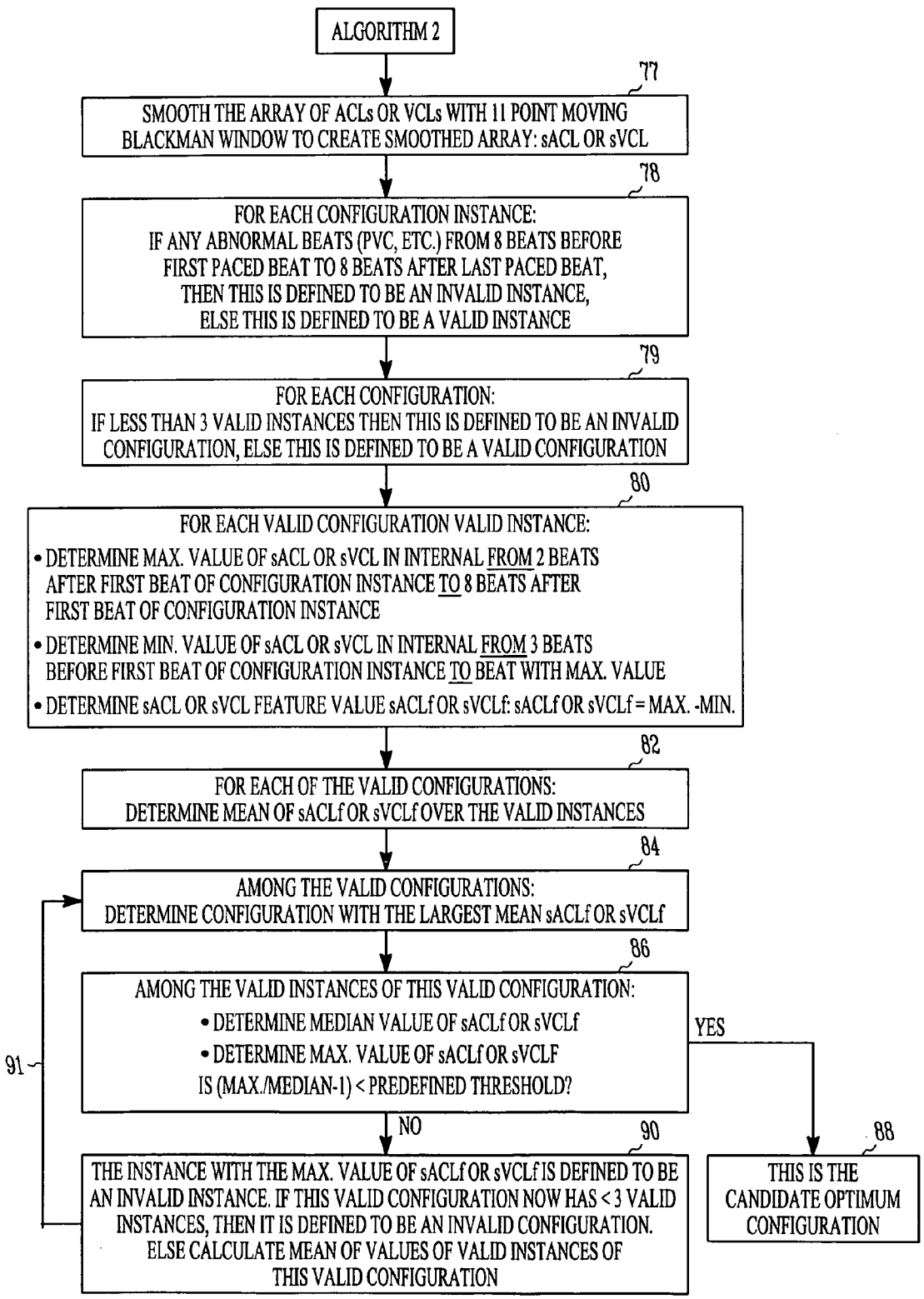

Algorithm 2 shown on FIG. 3C is executed to first select candidates for being the optimum configuration of pacing mode and inter-site delays. Here at block 77, the raw ACL data (or VCL data) are first smoothed using a known signal processing approach referred to as an 11 point moving Blackman window which yields a smoothed ACL array, (sACL). At block 78, a determination is made as to whether any abnormal beats, e.g., PVCs, occurred during an interval from eight beats before the first transient pace beat to 8 beats after the last transient paced beat. If abnormal beats are detected, the collected data is defined to be an "invalid instance". If no such abnormal beats occurred, it is defined to be a "valid instance". Next, and as reflected by block 79, for each configuration, a determination is made as to whether less than three "valid instances" occurred and, if so, it is defined to be an "invalid configuration". On the other hand, if three or more valid instances occur, it is defined to be a "valid configuration".

Figures 4, 5, 6:
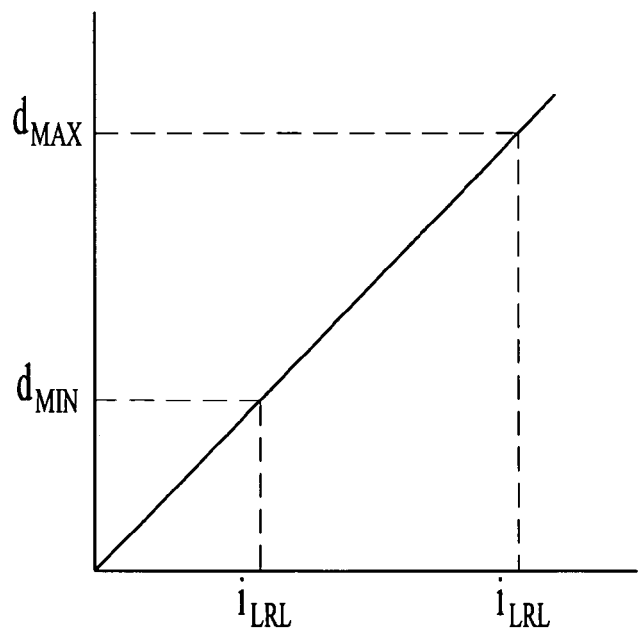
FIG. 4 is a representation of a series of baseline and paced beats useful in explaining the development of ACL features in accordance with a first algorithm.
FIG. 5 is a drawing similar to FIG. 4 for a second algorithm.
FIG. 6 is a plot of one dynamic delay v. cycle length relationship.

Next, as indicated by block 80, for each valid instance of a valid configuration, a determination is made as to the maximum value of sACL values in an interval from two beats after the first beat of a configuration instance to eight beats after the first beat of the configuration instance. Likewise, a minimum value of sACL values in an interval from three beats before the first beat of the configuration instance to the beat with the maximum value is determined. FIG. 5 is helpful in defining the respective intervals in which the maximum values and minimum values are to be found. Once the maximum value and minimum value in the respective intervals have been determined, a smoothed ACL feature value, referred to in the flow charts by the acronym sACLf, is computed as the maximum value minus the minimum value.

Upon completion of step 80, for each of the valid configurations of mode and inter-site delays, the mean of the sACLf values over the number of valid instances of a given configuration is computed. See block 82. Next, out of the previously determined valid configurations, the configuration exhibiting the largest mean sACLf is computed (block 84).

Once the particular configuration exhibiting the largest mean sACLf is determined, via step 84, the number of valid instances where the particular valid configuration has been repeated are examined to determine a median value and a maximum value of the smoothed ACL feature, sACLf. With the median and maximum values so determined, a test is made to determine whether the quantity (MAX/MEDIAN−1) is less than a predefined threshold. The purpose of this threshold test is to remove a MAX whose value is too large (relative to the median value). The "predefined threshold" has been determined empirically from data accumulated from a significant number of patients as a value of 9.5, which gave good results for the set of patients investigated.

If the result of the test is true, a potential candidate for the optimum configuration has been found (block 88). However, if the test at block 86 had proved false, the instance with the maximum value of sACLf is defined to be an invalid instance. If this valid configuration now has less than three valid instances, then it is defined to be an invalid configuration. If the valid configuration has three or more valid instances, the mean of values of valid instances are calculated for the valid configuration. Control then loops back over line 91 to block 84 to again repeat steps 84 and 86 until such time as the test set out in block 86 comes out "true".

Figure 3D:
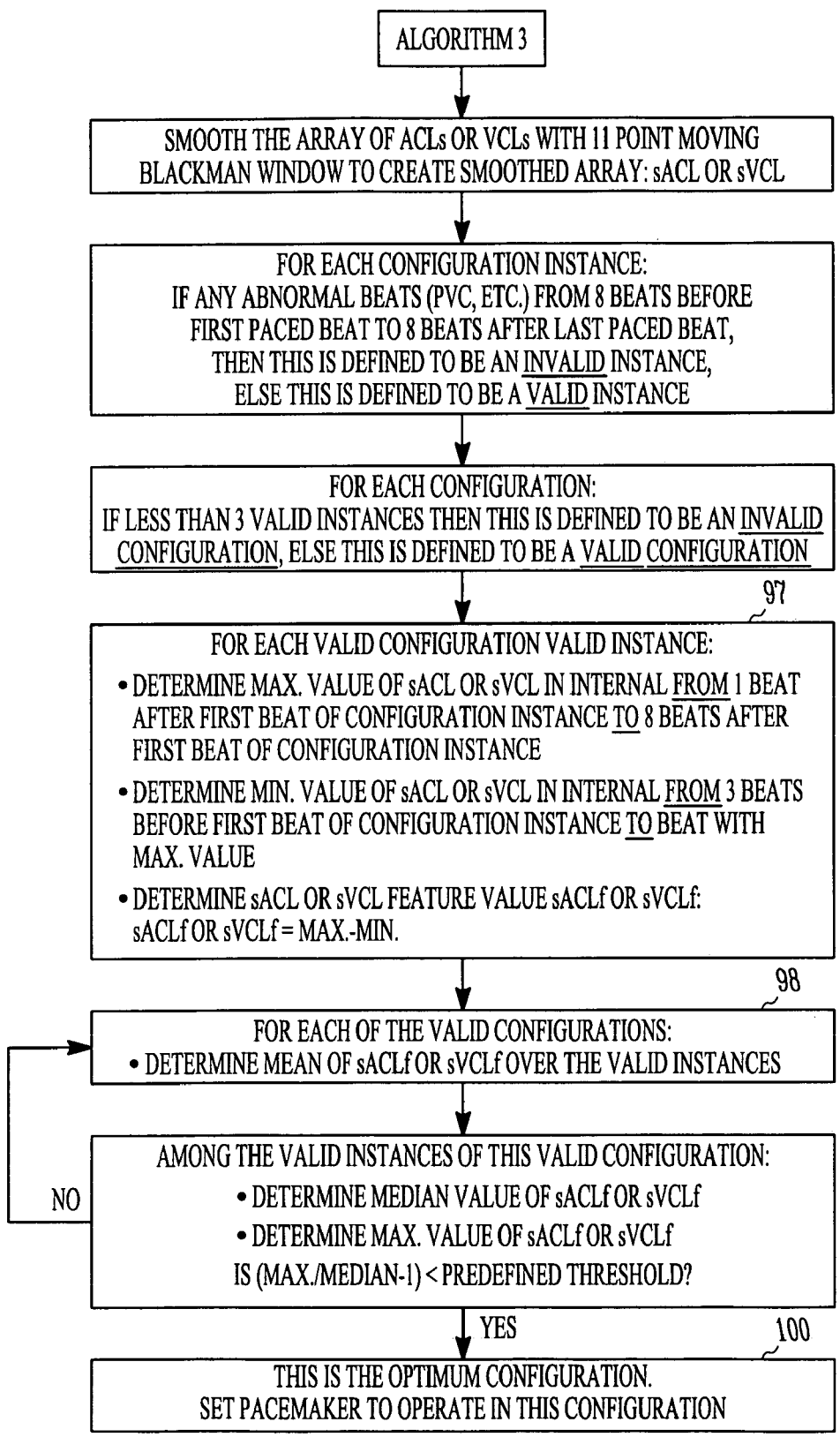

Referring again to the flow diagram of FIG. 3A, after all candidates for the optimum configuration have been determined, further processing takes place to determine which of the candidates is the optimum configuration so that the pacemaker can be programmed to operate in this configuration. Specifically, a test is made at block 92 to determine whether the largest mean sACLf computed at block 82 is less than 8.1 milliseconds. If it is, algorithm 1 of FIG. 3B is executed. If not, a further test is made to determine whether the largest mean sACLf value is greater than 29.0 milliseconds. If so, algorithm 3 illustrated at FIG. 3D is executed. If the largest mean sACLf feature value lies between 8.1 milliseconds and 29.0 milliseconds, it is the optimum configuration and, as indicated by block 96, the pacemaker is programmed to operate with that configuration of pacing mode and AV delay. The 8.1 ms and 29.0 ms values have been empirically established by study of data obtained from a set of ten patients in a study.

Referring next to FIG. 3B, the details of Algorithm 1 will be further explained. The first step in Algorithm 1 is identified by block 66 and involves smoothing the array of ACLs with a 3-point moving rectangle window. The resulting sACLf values are then also stored in the RAM memory. While other smoothing techniques are known to persons skilled in signal processing, a 3-point moving rectangle moving technique proves to be simple to execute and produces reliable results.

As was the case with algorithm 2, tests are made to determine whether any abnormal beats occurred in the interval from 8 beats before a first paced transient beat to 8 beats after the last paced transient beat for each of the configuration instances and if such an abnormal beat did occur, that configuration instance would be determined to be invalid. Then, each configuration is examined to determine if three or more valid instances were found in that configuration and, if so, it would be defined to be valid. However, if a configuration was found to include less than three valid instances, it would be defined as an invalid configuration.

Next, and as is reflected by block 68 in the flow diagram of FIG. 3B, for each valid instance of each valid configuration, the maximum value and the minimum value of the smooth ACL in an interval from two beats after the first beat of the configuration instance to seven beats after the first beat of the configuration instance are computed. This operation is further explained with the aid of FIG. 4. In FIG. 4, there is shown a series of 15 baseline beats, followed by five paced beats of an instance of a first configuration identified as C, again followed by another series of 15 baseline beats. The interval in which the maximum and minimum values of smoothed ACLs are to be located is labeled "MAX and MIN". Likewise, the interval in the which the mean value of the smoothed ACLs is to be located is identified by "MEAN". By selecting the intervals in the manner indicated, changes in ACL of a transient nature as distinguished from steady state is guaranteed. Once the MAX and MIN values of sACL for the configuration instance are known, a test is made to determine whether the absolute value of the quantity (MAX−MEAN) is greater than the absolute value of the quantity (MIN−MEAN) for the configuration instance. If the outcome of the test is true, then the smoothed ACL feature (sACLf) for the configuration instance is determined to be the quantity (MAX−MEAN). If the test is false, then sACLf is made to be (MIN−MEAN). See steps 70 and 72 in block 68.

Next, as is indicated by operation block 74, for each of the valid configurations, a computation is made to determine the average or mean of the sACLf over the number of valid instances of that configuration. Once the operation indicated by block 74 has been completed, the particular valid configuration exhibiting the greatest mean of smoothed ACL features is identified, as the pacemaker is automatically programmed to operate with this optimum configuration. See block 76.

Referring again to FIG. 3A, if the test at block 94 had established that the largest mean sACLf had been greater than 29.0 milliseconds, algorithm 3 shown in FIG. 3D would have been executed rather than algorithm 1. Referring to FIG. 3D, the steps therein are substantially identical to those of algorithm 2 shown in FIG. 3C except that in block 97 of FIG. 3D corresponding to block 80 in FIG. 3C, the maximum value of sACL (or sVCL) is determined at an interval of from one beat after the first beat of a configuration instance rather than from two beats after a first beat configuration instance. Secondly, block 100 in algorithm 3 shown in FIG. 3D differs from block 88 of algorithm 2 shown in FIG. 3C in that rather than identifying a candidate optimum configuration, the actual optimum configuration is established and the pacemaker is then programmed to operate in this optimum configuration.

Figure 3E:
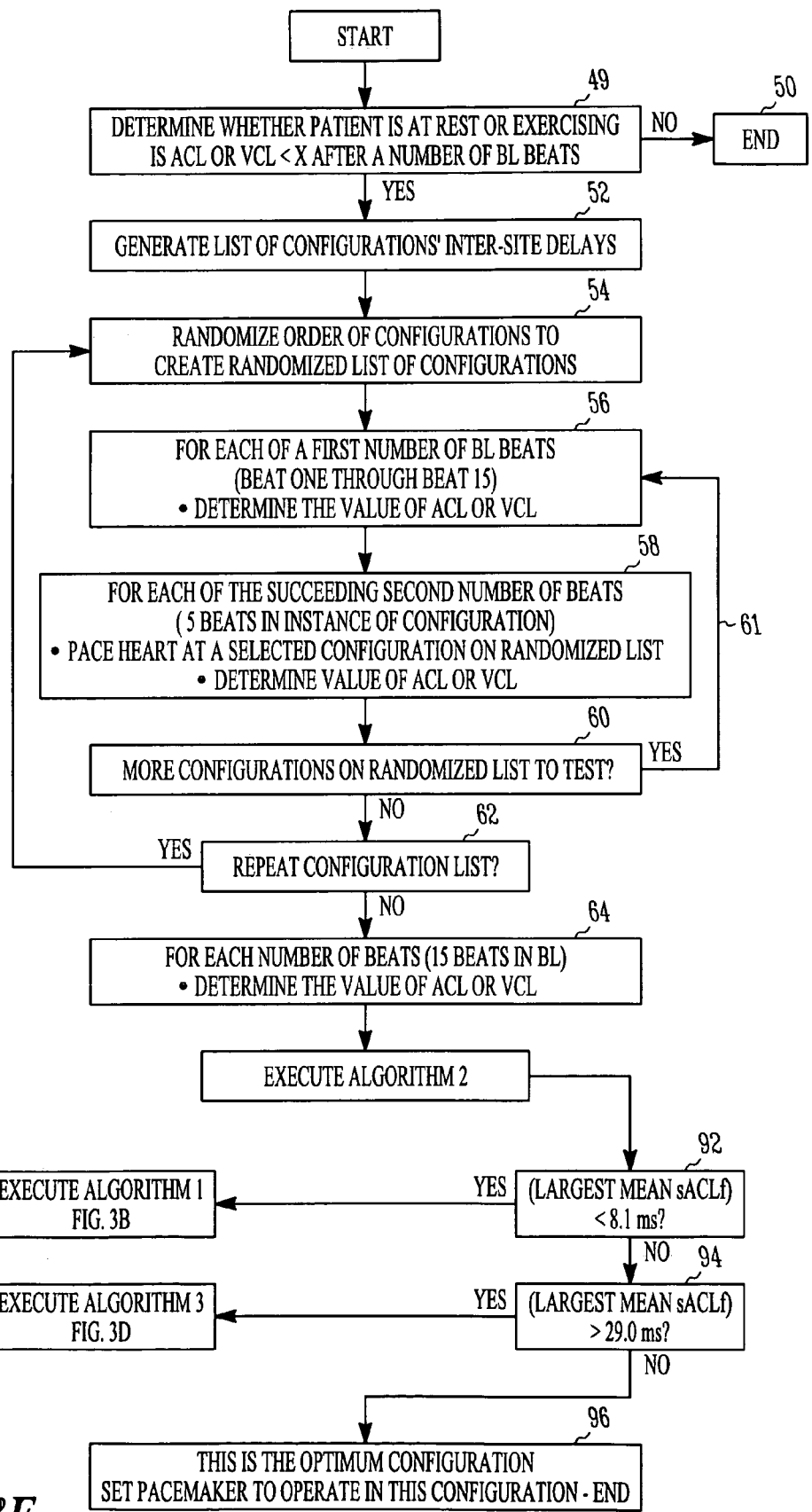

The above optimization is designed to be accomplished when the patient is asleep or otherwise in a sedentary state. The optimization algorithm, however, is also useful in optimizing pacing of the same individual during physical activities. This is illustrated in the flow diagram of FIG. 3E which differs from FIG. 3A only slightly. First, a determination is made at 49 based on intrinsic ACL or VCL (indicative of HR) as to whether the patient is exercising or at rest after a number of intrinsic beats are sensed. If the rate exceeds a predetermined limit, it is presumed that the patient is exercising. If it is determined that the patient is exercising, the algorithm of FIG. 3E is completed: otherwise the program ends at 50. The only difference in the determination in this situation is that the optimum pacing mode determined when the patient was at rest is retained and only the inter-site time delays are cycled and adjusted based on activity state. The result obtained yields an optimum dynamic value of the inter-site delays.

In accordance with one aspect of the invention, and in addition to the above, it has been found that in bi-ventricular pacing dynamic inter-site delay adjustments may be made on a beat-by-beat basis based on a linear function of the VCL or ACL. This relationship may be represented by the relation:

$$d_{vv} = mi_{vv} + b$$

$$m = \frac{d_{max} - d_{min}}{i_{lrl} - i_{url}}$$

$$b = d_{max} - mi_{lrl}$$

where
- $i_{lrl \text{ and } iurl}$ are the lower and upper rate limit intervals, the lower and upper rate limits having been set by the physician;
- $d_{max}$ and $d_{min}$ are the maximum and minimum interventricular delays for sequentially paced sites, one in each ventricle, which are also set by the physician based on the relative activity of the patient over time and which may be varied based on statistical activity trends of the patient;
- $i_{vv}$ is the ACL (VCL could also be used);
- $d_{vv}$ is the dynamic interventricular delay or the delay between sequentially paced sites, one in each ventricle.

In this manner, the $d_{vv}$ inter-site delay can be caused to vary linearly with the ventricular cycle length (or ACL). This is illustrated by the plot of FIG. 6. Alternatively, it is contemplated that a non-linear function may be used.

Thus, in accordance with the invention, patient tests have shown that the relatively easy-to-measure atrial cycle length (or ventricular cycle length) can be used to automatically determine the pacing mode and site-to-site delay configuration which provides pulse pressures greater than the pulse pressure achieved with baseline cardiac performance. The need for a special sensor to actually measure pulse pressure itself, which is difficult to measure, is eliminated.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. As already mentioned, the intrinsic and paced beat information can readily be telemetered out to an external programmer/monitor incorporating a microprocessor and associated memory so that the ACL determinations and signal processing thereof can be done external to the patient in arriving at the optimal pacing mode-AV delay interval. Hence, the scope of the invention is to be determined from the appended claims.

What is claimed is:

1. A method of optimizing the pacing mode and inter-site delay configuration in heart chambers having multiple pacing sites therein using a dual chamber pacemaker of the type having means for sensing atrial depolarization events, means for sensing ventricular depolarization events and means for applying cardiac stimulating pulses selectively to the right, left or both ventricular chambers at a plurality of sites in said right, left or both ventricular chambers at predetermined delay intervals following detection of atrial depolarization events, said method comprising:
   (a) tracking a patient's intrinsic atrial depolarization events;
   (b) measuring the patient's atrial cycle length (ACL) between successive atrial depolarization events over a first predetermined number of heart beats, $N_1$, establishing a first set of inter-site delay intervals and storing the measured ACLs as an array in a memory to establish a baseline value wherein said inter-site delay intervals involve a plurality of sites in a cardiac chamber and at least one cardiac chamber;

(c) changing at least one of one or more inter-site delay intervals and pacing mode configuration s for a second predetermined number of heart beats, $N_2$, less than the first predetermined number of heart beats by changing (i) the delay interval of the pacemaker between successive sites from the baseline value to a different delay interval;

(d) measuring the patient's ACLs between successive atrial depolarization events over the second predetermined number of heart beats and storing the measuring ACLs in the array in said memory;

(e) calculating and storing an ACL feature value obtained from the patient's atrial cycle length measured in (b) and (d);

(f) repeating (a)–(e) in iterative cycles over a range of inter-site delay intervals;

(g) after (f) for each pacing mode inter-site delay configuration calculating the average of the ACL features over all of the occurrences of the configuration;

(h) determining the optimal configuration from among the averages determined in (g); and (i) setting the inter-site delays and pacing mode configuration of the pacemaker to the optimal inter-site delays and pacing mode configuration established in (h).

2. A method as in claim 1 wherein the ACL feature value is calculated by:

(j) smoothing the array of ACLs;

(k) determining from the smoothed array of ACLs a maximum value and a minimum value in a first predetermined interval measured in beats for each inter-site delay and pacing mode configuration;

(l) determining from the smoothed array a mean value of ACLs in a second predetermined interval measured in beats for each inter-site delay and pacing mode configuration;

(m) computing an absolute value of the difference between said maximum value and said mean value and computing an absolute value of the difference between said minimum value and said mean value;

(n) comparing the absolute value of the difference between the maximum value and the mean value with the absolute value of the difference between the minimum value and the mean value to determine which is the larger; and (o) setting the ACL feature value to the difference between the maximum value and the mean value when the absolute value of that difference is greater than the absolute value of the difference between the minimum value and the mean value, and setting the ACL feature value to the difference between the minimum value and the mean value when the absolute value of the difference between the maximum value and the mean value is less than or equal to the absolute value of the difference between the minimum value and the mean value.

3. A method for optimizing delay intervals between pacing sites and pacing mode configuration in a cardiac chamber having a plurality of pacing cites therein using a programmable dual chamber cardiac pacemaker of the type having means for sensing atrial and ventricular depolarization events, including a microprocessor-based controller for using said plurality of pacing sites for selectively stimulating the right, the left or both ventricular chambers with pacing pulses at predetermined delay intervals following detection of atrial depolarization events, the microprocessor-based controller having means for determining atrial cycle lengths and a memory for storing data in an addressable array, said method comprising:

(a) storing in the memory a listing of pacing mode and inter-site delay configurations, each such configuration specifying ventricular chamber(s) to be stimulated and inter-site delay intervals to be utilized wherein said pacing mode and inter-site delay configurations involve a plurality of sites in a cardiac chamber and one or more chambers;

(b) pacing the ventricular chamber(s) in accordance with a pacing mode inter-site delay configuration selected randomly from said listing for a first number of beats, $N_1$, following a second number of intrinsic beats, $N_2$, sufficient to establish a base line;

(c) repeating (b) for each pacing mode and inter-site delay configuration contained in the listing;

(d) determining the ACL values between each of the $N_1$ and $N_2$ beats resulting from (b) and (c) and storing said ACL value in the addressable array in the memory;

(e) repeating (b) through (d) a predetermined number of instances, $N_3$;

(f) smoothing the array of ACLs;

(g) determining for all $N_3$ instances of each pacing mode and inter-site delay configuration the maximum value of the smoothed ACLs in a first interval beginning after a change to the first number of beats $N_1$ and ending after a change to the second number of beats, $N_2$, and a minimum value of the smoothed ACLs in a second interval beginning a predetermined number of beats prior to a change from the $N_2$ beats to the $N_1$ beats and ending with the beat associated with the maximum value;

(h) computing a smoothed ACL feature as the difference between the maximum value and the minimum value;

(i) calculating the mean value of the smoothed ACL features computed in (h) over the $N_3$ instances for each pacing mode inter-site delay configuration and determining the configuration yielding the largest mean value;

(j) determining among the $N_3$ instances associated with the configuration yielding the largest mean value a median value and a maximum value of smoothed ACL features; and (k) programming the pacemaker to the configuration determined in (i) when the difference between the ratio of maximum value and the median value is less than a predetermined value.

4. A method as in claim 3 and when the ratio of maximum value and the median value of smoothed ACL features is greater than or equal to the predetermined threshold value, repeating (i) and (j) after recalculating the mean of the instances of the configuration associated with the largest mean value of smoothed ACL features after removing the instance having the maximum value of smoothed ACL features from the instances.

5. A method for optimizing inter-site delay intervals and pacing mode configuration of a programmable, dual-chamber, cardiac pacemaker of the type having means for sensing atrial and ventricular depolarization events, including a microprocessor-based controller using a plurality of pacing sites for selectively stimulating the right and left ventricular chambers with pacing pulses at predetermined inter-site delay intervals following detection of atrial depolarization events, the microprocessor-based controller having means for determining atrial cycle lengths (ACLs) or ventricular cycle lengths (VCLs) and a memory for storing data in an addressable array, said method comprising:

(a) establishing an upper rate limit and a lower rate limit for pacing and storing these in memory;
(b) establishing a range of allowable delay intervals between pacing the right ventricle and pacing a first site in the left ventricle in relation to said upper rate limit and said lower rate limit; and
(c) making dynamic inter-site delay interval adjustments to optimize the interval based on a linear relationship between the delay interval between adjacent pulses in the right and left ventricles and the VCL or ACL, wherein said inter-site delay interval is adjusted between maximum and minimum values in said range of allowable delay intervals wherein said inter-site delay intervals involve a plurality of sites in at least one cardiac chamber.

6. A method according to claim 5 wherein said adjustments are made on an on-going basis.

7. A method of enhancing paced cardiac performance by optimizing the operation of a pacing device, said method comprising:

(a) measuring a selected cardiac performance parameter indicative of the performance of a patient's heart during multi-site pacing to establish a baseline using a first pacing device operation setting wherein said multi-site pacing involves a plurality of sites in a cardiac chamber and at least one chamber;
(b) varying the operation setting;
(c) measuring said parameter during pacing using a changed operation setting; and
(d) determining an optimal pacer device operation setting based on measurements of said parameter at a plurality of settings.

8. A method of enhancing paced cardiac performance by optimizing the operation of a pacing device, said method comprising:

(a) measuring a selected cardiac performance parameter indicative of the performance of a patient's heart during multi-site pacing to establish a baseline using a first setting comprising a first pacing mode and first inter-site delay interval wherein said multi-site pacing involves a plurality of sites in a cardiac chamber and at least one cardiac chamber;
(b) varying the setting by changing an inter-site delay interval or pacing mode;
(c) measuring said parameter during pacing using a changed setting; and
(d) determining an optimal inter-site delay interval and pacing mode configuration based on measurements of said parameter at a plurality of settings.

9. The method of claim 8 comprising:

(e) after (c), for each pacing mode inter-site delay interval and mode configuration used, calculating an average value of the selected parameter of interest;
(f) determining an optimal inter-site delay interval and pacing mode configuration from among the averages determined in (e); and
(g) setting the inter-site delays and pacing mode configuration of the pacemaker to the optimal inter-site delay pattern and pacing mode configuration established in (f).

10. A method as in claim 8 wherein said selected cardiac performance parameter of interest is selected from the group consisting of atrial cycle length (ACL), ventricle cycle length (VCL), ventricular volumes, blood flow velocity, total acoustic noise and direct measurement of pulse pressure.

11. A method as in claim 10 wherein a plurality of selected cardiac performance parameters of interest are employed in obtaining an optimal inter-site delay pattern and pacing mode configuration.

12. A method as in claim 10 including performing said optimization method with respect to an exercising patient.

13. A method of enhancing one or more aspects of cardiac performance by optimizing pacing mode configuration and/or inter-site delay pattern in a programmable multi-chamber, multi-site per chamber, pacemaker said method comprising:

(a) selecting a cardiac parameter of interest of known relation to an aspect of cardiac performance; and
(b) comparing a plurality of inter-site delay patterns and/or pacing mode configurations in a manner which determines the optimum delay pattern and pacing mode to optimize said parameter and thereby optimize said aspect of cardiac performance, wherein said pacing mode configurations and inter-site delay patterns include a plurality of sites in each of at least one cardiac chamber.

* * * * *

UNITED STATES PATENT AND TRADEMARK OFFICE
CERTIFICATE OF CORRECTION

PATENT NO. : 7,194,305 B1  
APPLICATION NO. : 09/545536  
DATED : March 20, 2007  
INVENTOR(S) : Salo et al.

Page 1 of 1

It is certified that error appears in the above-identified patent and that said Letters Patent is hereby corrected as shown below:

Column 11, line 7, in claim 1, delete "configuration s" and insert --configurations --, therefor.

Column 11, line 63, in claim 3, delete "cites" and insert -- sites --, therefor.

Signed and Sealed this

Twelfth Day of June, 2007

JON W. DUDAS  
*Director of the United States Patent and Trademark Office*